(12) United States Patent
Chou

(10) Patent No.: US 7,856,674 B2
(45) Date of Patent: Dec. 28, 2010

(54) BUCKLE DEVICE FOR SWIMMING/DIVING GOGGLES

(76) Inventor: Terry Chou, No. 12, Hsin Ho Herng Road, Tainan City (TW)

( * ) Notice: Subject to any disclaimer, the term of this patent is extended or adjusted under 35 U.S.C. 154(b) by 720 days.

(21) Appl. No.: 11/935,543

(22) Filed: Nov. 6, 2007

(65) Prior Publication Data
US 2009/0113608 A1 May 7, 2009

(51) Int. Cl.
*A61F 9/02* (2006.01)
(52) U.S. Cl. .......................................................... 2/452
(58) Field of Classification Search .................... 2/430, 2/448, 452; 24/199
See application file for complete search history.

(56) References Cited

U.S. PATENT DOCUMENTS

| | | | |
|---|---|---|---|
| 5,956,778 A * | 9/1999 | Godoy | 2/428 |
| 7,185,373 B2 * | 3/2007 | Chiang | 2/445 |
| 7,251,842 B1 * | 8/2007 | Chiang | 2/445 |
| 7,296,306 B2 * | 11/2007 | Chou | 2/448 |

* cited by examiner

*Primary Examiner*—Katherine Moran
(74) *Attorney, Agent, or Firm*—Banger Shia

(57) ABSTRACT

A pair of swimming/diving goggles includes a main body and two head strap coupling members respectively provided on two sides of the main body. A board is pivotably mounted in a through-hole in each head strap coupling member. A head strap is extended through the through-hole of each head strap coupling member and around the board. A spacing between the board and the outer end wall of the through-hole of each the head strap coupling member is changeable when the board is pivoted, allowing the head strap to move to adjust a tightening length of the head strap. The head strap exerts a clamping force to clamp the head strap between the board and the outer end wall of the through-hole.

9 Claims, 13 Drawing Sheets

A-A

BUCKLE DEVICE FOR SWIMMING/DIVING GOGGLES

BACKGROUND OF THE INVENTION

The present invention relates to a buckle device and, more particularly, to a buckle device for a pair of swimming/diving goggles that provides a reliable clamping effect for a head strap of the pair of swimming/diving goggles and that allows easy adjustment of the head strap.

FIG. 10 shows an exploded perspective view of a conventional buckle 1' for swimming/diving goggles. FIG. 11 shows a partial top view, partially sectioned, of a pair of swimming/diving goggles utilizing the buckle 1' of FIG. 10. The buckle 1' is made of a rigid material and includes a connecting portion 11' on an end thereof for connecting with a main body 3' of the pair of swimming/diving goggles. A tying portion 12' is provided on the other end of the buckle 1' for connecting with an end of a head strap 2' made of a soft material. The tying portion 12' includes two posts 121' and 122' and a notch 123' in an outer end thereof. The end of the head strap 2' is wound around the posts 121' and 122' and finally inserted into a space between the notch 123' and the posts 121', thereby fixing the tightening length of the head strap 2'.

When adjusting the tightening length of the head strap 2', the user has to remove the pair of swimming/diving goggles from his/her head, loosen the head strap 2' at the posts 121' and 122' and the notch 123', adjust the head strap 2', and then put the pair of swimming/diving goggles back on his/her head. If the tightness of the head strap 2' is not appropriate, the whole adjusting procedure has to be repeated again and again until an appropriate tightness for the user is reached. Further, the head strap 2' is apt to bend and deform due to double winding through the posts 121' and 122'. Further, the buckle 1À and the main body 3' are separate elements and, thus, liable to move relative to each other while failing to provide an integral appearance. Further, the connecting portion 11' may be disengaged from the main body 3' when impacted.

U.S. Pat. No. 6,691,378 discloses a buckle device to allow easy adjustment of a head strap of a pair of swimming/diving goggles and to provide a reliable clamping effect for the head strap. As illustrated in FIGS. 12-14 of the drawings, the buckle device includes a body 4' having a pressing portion 41' on an end thereof and a clamping portion 42' on the other end thereof. The pressing portion 41' and the clamping portion 42' are connected together by a connecting portion 43' that is thinner and bendable. The pressing portion 41' includes two sidewalls and a post 411' fixed between the sidewalls. A release section 412' extends from an end of the pressing portion 41' to allow manual operation for adjusting the head strap 5'. The clamping portion 42' includes a clamping hole 421' through which the head strap 5' extends. A retaining edge 422' is formed on a top edge of each of two lateral walls defining the clamping hole 421'.

In assembly, the connecting portion 43' is wound around a mounting peg 61' of a main body 6' of the pair of swimming/diving goggles, with the pressing portion 41' being located on an outer side of the main body 6'. An end of the head strap 5' is extended into the body 4' via the clamping hole 421', wound around the post 411', and then extended out of the body 4' via the clamping hole 421'. When adjustment of the head strap 5' is required, the user directly pulls the distal end 51' of the head strap 5' that until the required tightness and length of the head strap 5' are obtained.

With reference to FIG. 13, when the head strap 5' is released, the inner portion 52' of the head strap 5' exerts a pulling force on the post 411' of the pressing portion 41'. Thus, the post 411' moves to a position where the head strap 5' is tightly positioned by the post 411' and the retaining edge 422'. With reference to FIG. 14, when the post 411' is moved to disengage from the retaining edge 422', the inner portion 52' of the head strap 5' can be pulled to release the head strap 5'.

However, the body 4' of the buckle device and the main body 6' of the pair of swimming/diving goggles are separate elements and, thus, liable to move relative to each other (see phantom lines in FIG. 12) while failing to provide an integral appearance. Further, the movable post 411À complicates the buckle device and can not be operated easily when loosening of the head strap 5' is required.

BRIEF SUMMARY OF THE INVENTION

An objective of the present invention is to provide a buckle device that allows easy adjustment of the head strap while providing a reliable clamping effect for the head strap.

A pair of swimming/diving goggles according to the preferred teachings of the present invention includes a main body and two head strap coupling members respectively provided on two sides of the main body. Each head strap coupling member includes a through-hole defined by two lateral walls and an outer end wall. The pair of swimming/diving goggles according to the preferred teachings of the present invention further includes two adjusting blocks each including a board pivotably mounted in the through-hole of one of the two head strap coupling members, allowing the board to pivot relative to the main body. A head strap made of a soft, elastic material is extended through the through-hole of each head strap coupling member and around the board of each adjusting block, with a portion of the head strap being located between the outer end wall of the through-hole and the board. A spacing between the board of each adjusting block and the outer end wall of the through-hole of one of the head strap coupling members is changeable when one of the adjusting blocks is pivoted, allowing the head strap to move to adjust a tightening length of the head strap. The head strap exerts a clamping force to clamp the head strap between the board and the outer end wall of the through-hole.

In an example, the head strap coupling members are integrally formed with the main body as a single continuous monolithic piece.

In another example, each head strap coupling member includes a coupling portion, and each side of the head strap coupling members includes a coupling portion releasably coupled with the coupling portion of one of the head strap coupling members.

In an example, each lateral wall of the through-hole includes a groove, and the board of each adjusting block includes two pivots respectively and pivotably received in the grooves. The outer end wall of the through-hole of each head strap coupling member includes a pressing edge having a width smaller than that of the outer end wall. The head strap is securely clamped between the pressing edge of each head strap coupling member and the board of each adjusting block. The board of each adjusting block further includes an operative piece extending from an outer end of the board in a direction transverse to the board. The operative piece includes an opening through which the head strap extends. The board of each adjusting block further includes a stop wall on each of two lateral sides thereof, and the head strap is located between the stop walls. Each lateral wall of the through-hole of each head strap coupling member includes a stop edge. The stop walls of each adjusting block abut with the stop edges of one of the head strap coupling members to restrain the spacing between the outer end wall of the through-hole and the board.

In a further example, a cover is mounted to each head strap coupling member and coves the through-hole.

The present invention will become clearer in light of the following detailed description of illustrative embodiments of this invention described in connection with the drawings.

DESCRIPTION OF THE DRAWINGS

The illustrative embodiments may best be described by reference to the accompanying drawings where.

Figure 1:
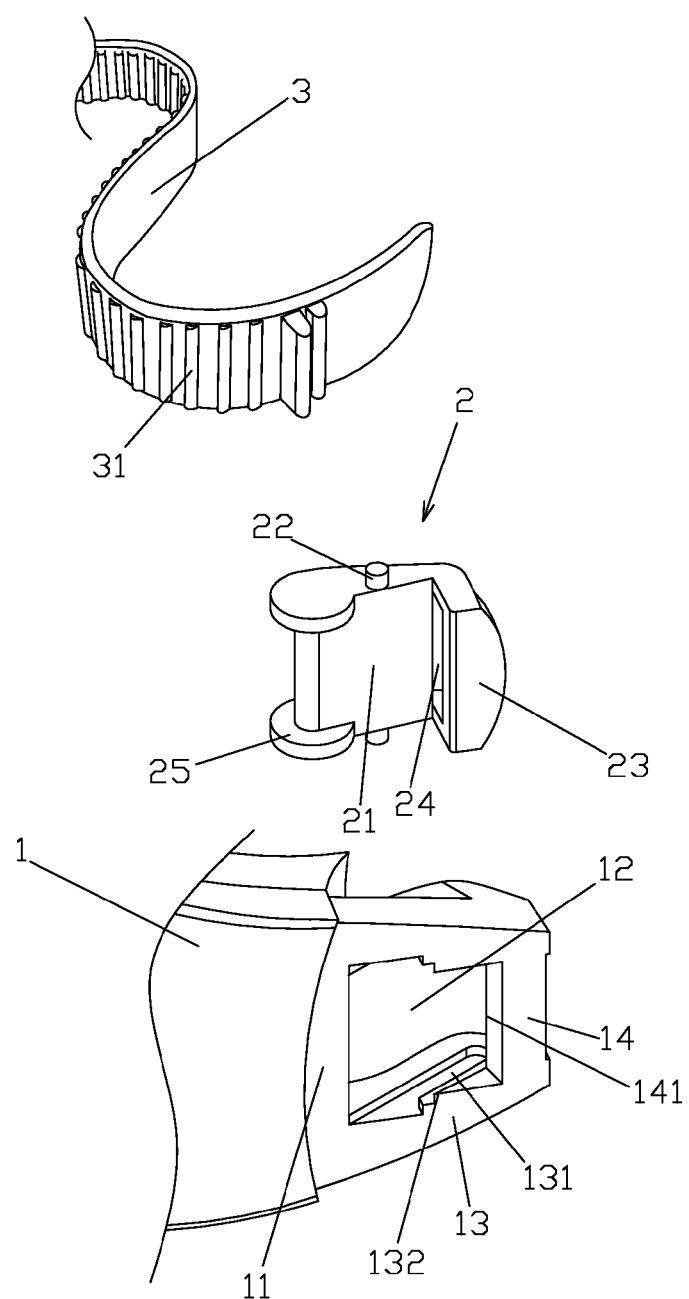
FIG. 1 shows a partial, exploded perspective view of an example of a pair of swimming/diving goggles according to the preferred teachings of the present invention.

All figures are drawn for ease of explanation of the basic teachings of the present invention only; the extensions of the Figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

An example of a pair of swimming/diving goggles according to the preferred teachings of the present invention is shown in FIGS. 1-5 of the drawings. The pair of swimming/diving goggles includes a main body 1, two adjusting blocks 2 (only one is shown), and a head strap 3. Elements that may be mounted to the main body 1 include but not limited to one or two rigid lenses, one or two soft lens-receiving members, a bridge, and two nose pads. A head strap coupling member 11 is directly formed on each of two sides of the main body 1. In the example shown, the head strap coupling members 11 are integrally formed with the main body 1 as a single continuous monolithic piece. Each head strap coupling member 1 includes a through-hole 12. Each of two lateral walls 13 defining the through-hole 12 includes a groove 131 and a stop edge 132 intermediate the groove 131 and an outer end wall 14 defining the through-hole 12. The outer end wall 14 includes a pressing edge 141 having a width smaller than the outer end wall 14.

Each adjusting block 2 is mounted in the through-hole 12 of one of the head strap coupling members 1 and made of a rigid material. Each adjusting block 2 includes a board 21 having a pivotal mechanism in the preferred form shown as two pivots 22 formed on two lateral sides of the board 21 and pivotably received in the grooves 131. An operative piece 23 extends from an outer end of the board 21 in a direction transverse to the board 21. The operative piece 23 includes an opening 24 extending from an outer face thereof through an inner face thereof and facing an inner side of the board 21. A stop wall 25 is formed on an inner end of each of the lateral sides of the board 21.

The pair of swimming/diving goggles further includes a head strap 3 made of a soft, elastic material. The head strap 3 includes a plurality of spaced teeth 31 on a side thereof.

Figure 2:
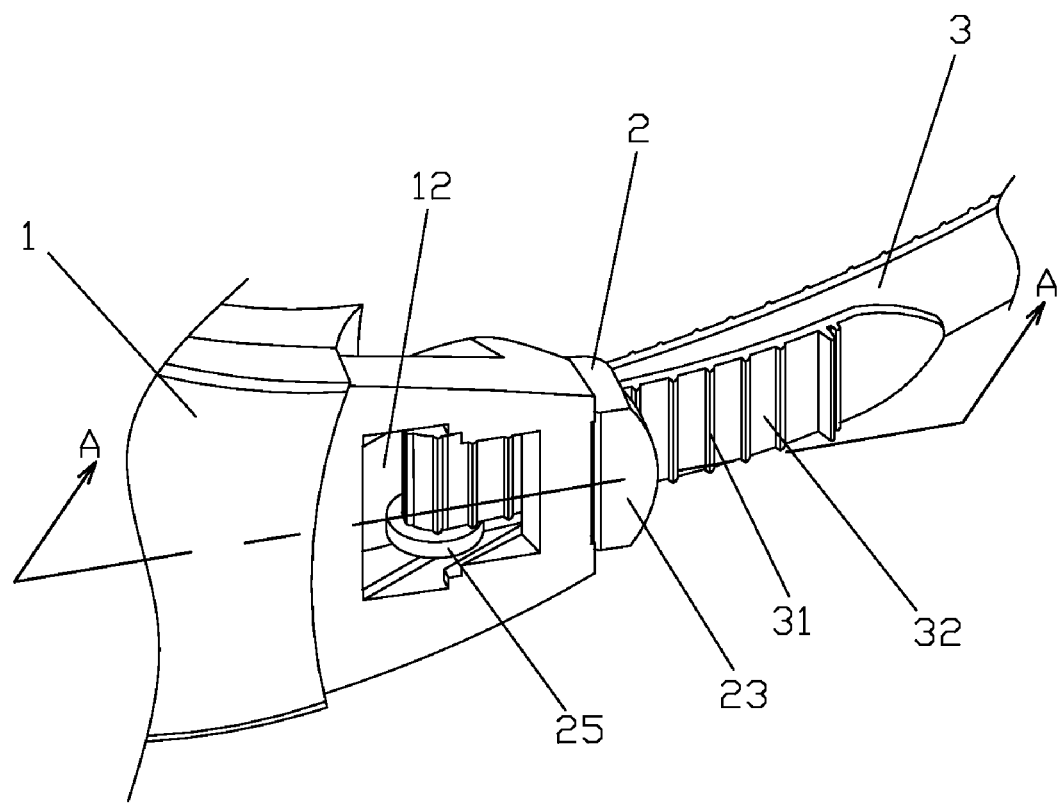
FIG. 2 shows a partial, perspective view of the pair of swimming/diving goggles of FIG. 1.
Figure 3:
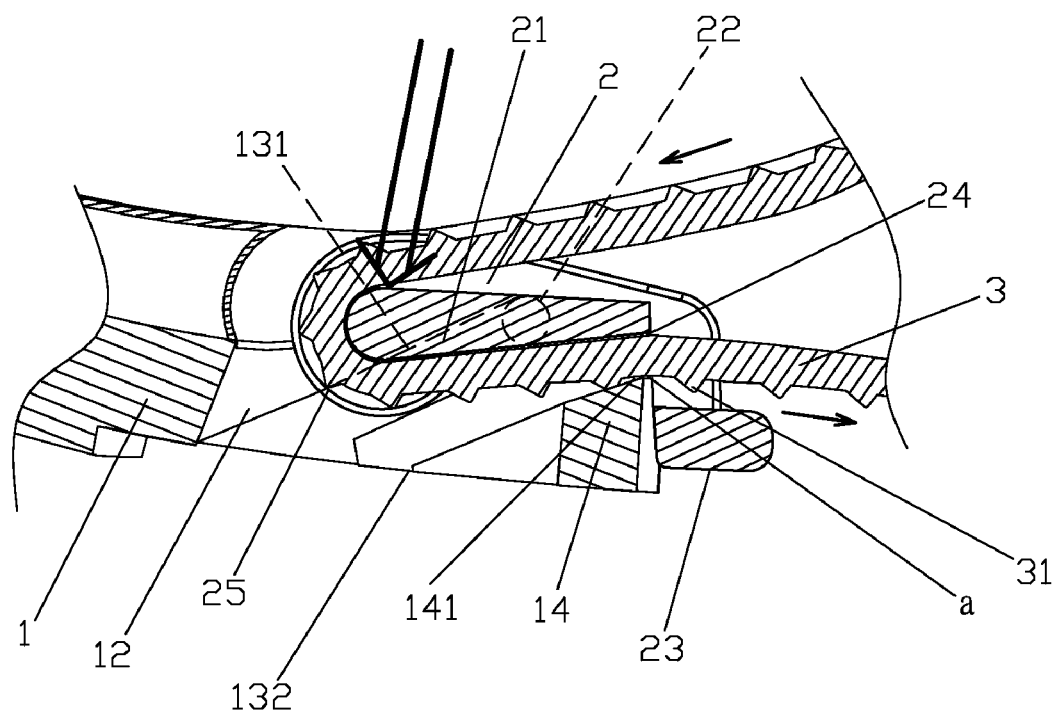
FIG. 3 shows a partial, cross sectional view of the pair of swimming/diving goggles of FIG. 2 according to section line A-A of FIG. 2, illustrating adjustment of tightness of a head strap.

With reference to FIGS. 1, 2, and 3, in assembly, the adjusting blocks 2 are mounted into the through-holes 12 of the main body 1, with the pivots 22 received in the grooves 131, and with each operative piece 23 abutting with an outer side of the outer end wall 14 of one of the head strap coupling members 11. Thus, each adjusting block 2 is pivotable relative to the main body 1 to change a spacing ÀaÀ between the board 21 and the pressing edge 141. Each of two ends of the head strap 3 is then extended through the through-hole 12 in one of the head strap coupling members 11, wound around one of the boards 21, and extended out of the main body 1 through the opening 24 of one of the operative pieces 23. Some of the teeth 31 of the head strap 3 are located between the board 21 and the outer end wall 14 of the through-hole 12. Furthermore, the head strap 3 is located between the stop walls 25 of the board 21 to prevent movement of the head strap 3 in the transverse direction while allowing smooth adjustment.

With reference to FIG. 3, when adjustment of the length (or tightening length) of the head strap 3 is required while the pair of the swimming/diving goggles is worn on a user, the user can directly pull an outer section 32 of the head strap 3 to cause the adjusting block 2 to pivot about a pivot axis defined by the pivots 22. The inner end of the adjusting block 2 moves relative to the main body 1 in a direction indicated by the double arrow in FIG. 3. Thus, the spacing ÀaÀ is increased to allow smooth, outward pulling of the head strap 3 for the purposes of clamping the head of the user.

Figure 4:
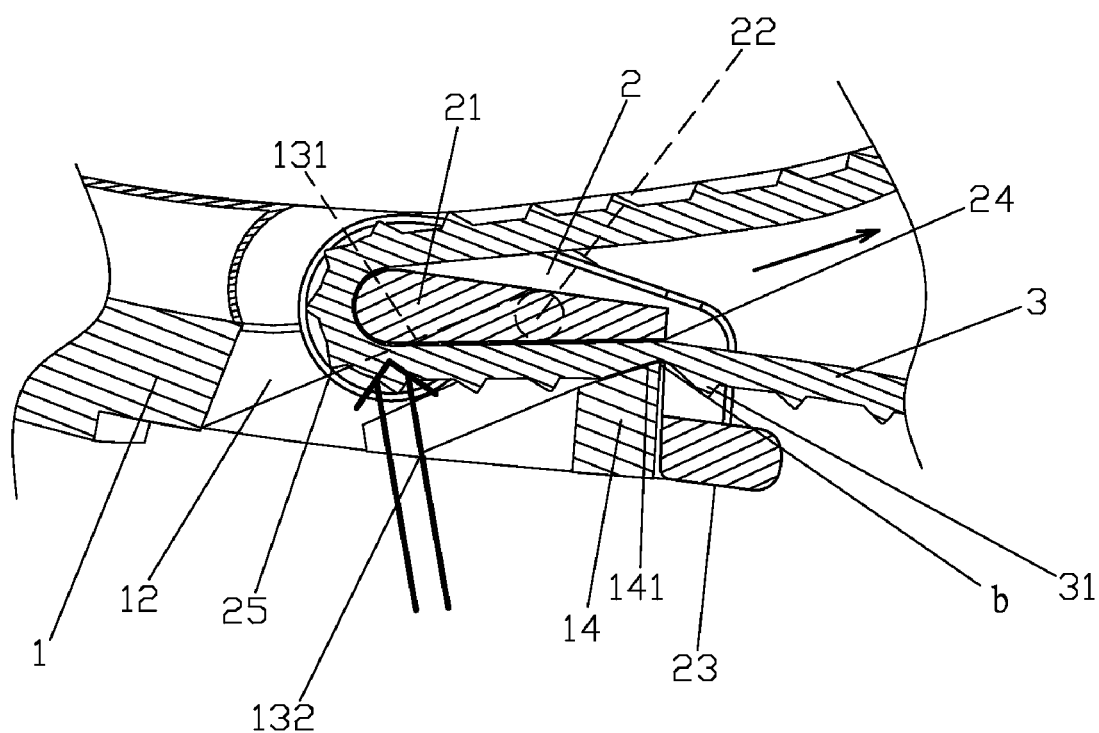
FIG. 4 is a view similar to FIG. 3, illustrating clamping of the head strap.

When the head strap 3 is released, the clamping force of the head strap 3 acts in a direction indicated by the single arrow shown in FIG. 4. Thus, the inner section of the board 21 is pressed by the clamping force, and the spacing (now designated by ÀbÀ) between the board 21 and the pressing edge 141 of the outer end wall 14 becomes smaller. As a result, the head strap 3 is clamped in place. The larger the clamping force, the larger the force imparted to the board 21 to clamp the head strap 3. Accordingly, the head strap 3 can be reliably clamped after adjustment of length.

Figure 5:
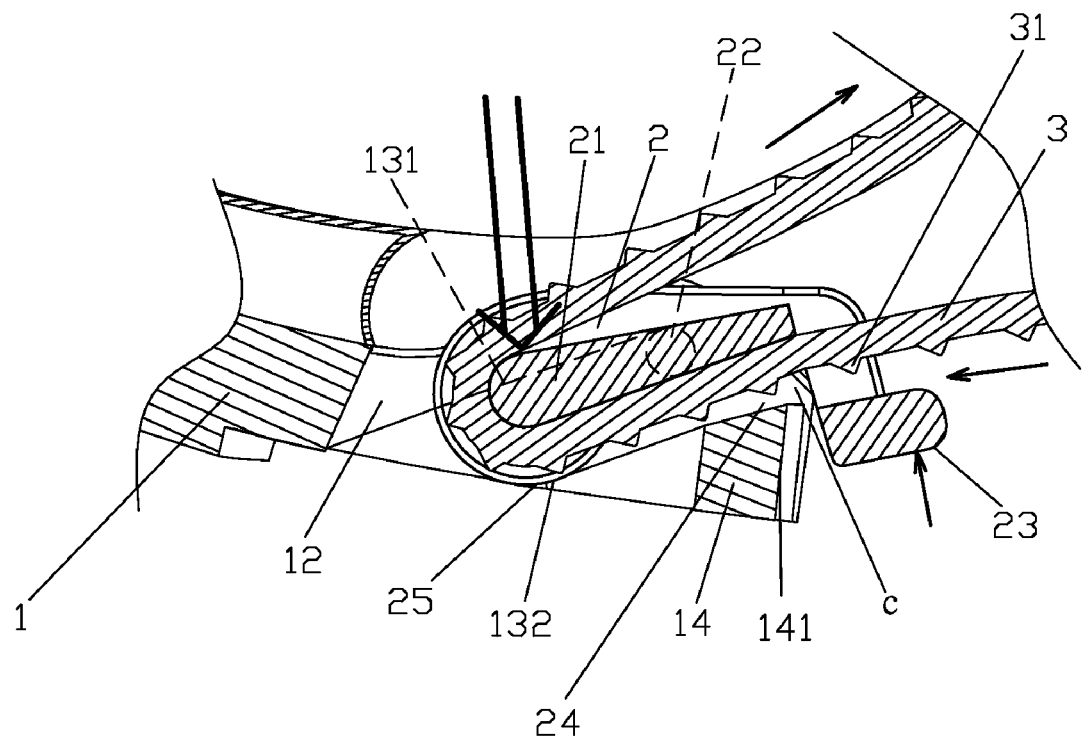
FIG. 5 is a view similar to FIG. 4, illustrating loosening of the head strap.

With reference to FIG. 5, when loosening of the head strap 3 is required, the user presses the operative piece 23 to increase the spacing (now designated by ÀcÀ) between the board 21 and the pressing edge 141 of the outer end wall 14. The board 21 pivots in a direction indicated by the double arrow head in FIG. 5. The movement of the adjusting block 2 is stopped when the stop walls 25 come into contact with the stop edges 132, preventing the adjusting block 2 from pressing against the head of the user and preventing excessive clamping force imparted to the head strap 3 resulting from pressing by the adjusting block 2. Smooth operation is, thus, provided. The head strap 3 in this state can be pulled in the reverse direction to loosen the head strap 3.

Figure 6:
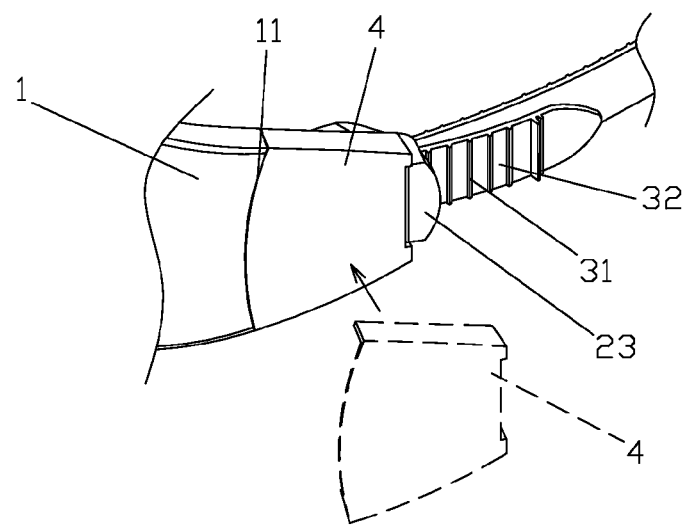
FIG. 6 shows a partial, perspective view of another example of the pair of swimming/diving goggles according to the preferred teachings of the present invention.

With reference to FIG. 6, a cover 4 can be mounted to each head strap coupling member 11 to cover the through-hole 12.

Figure 7:
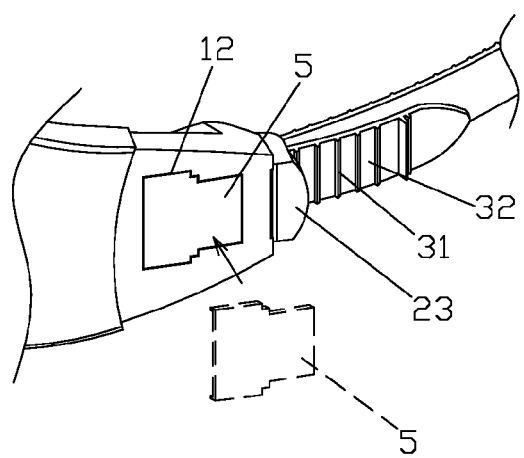
FIG. 7 shows a partial, perspective view of a further example of the pair of swimming/diving goggles according to the preferred teachings of the present invention.

With reference to FIG. 7, a cover 5 corresponding to the shape of the through-hole 12 can be mounted to each head strap coupling member 11 to provide an aesthetic appearance.

Figure 8:
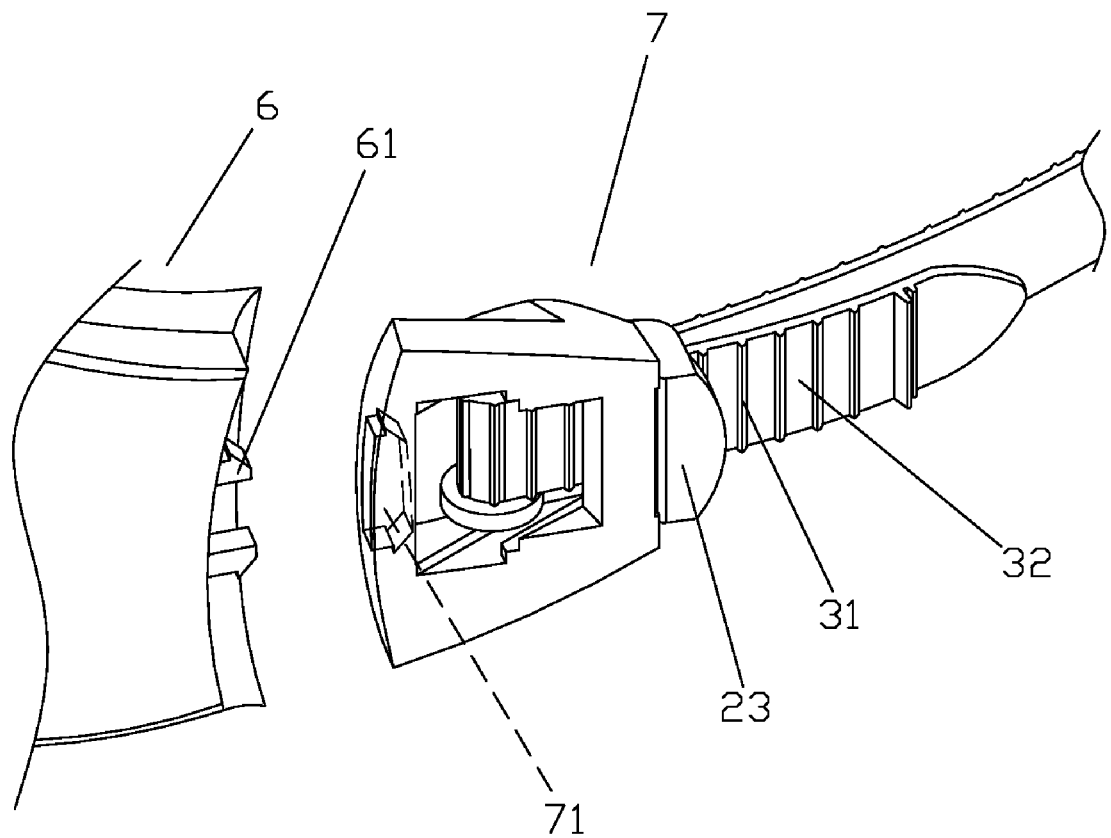
FIG. 8 shows a partial, exploded perspective view of still another example of the pair of swimming/diving goggles according to the preferred teachings of the present invention.
Figure 9:
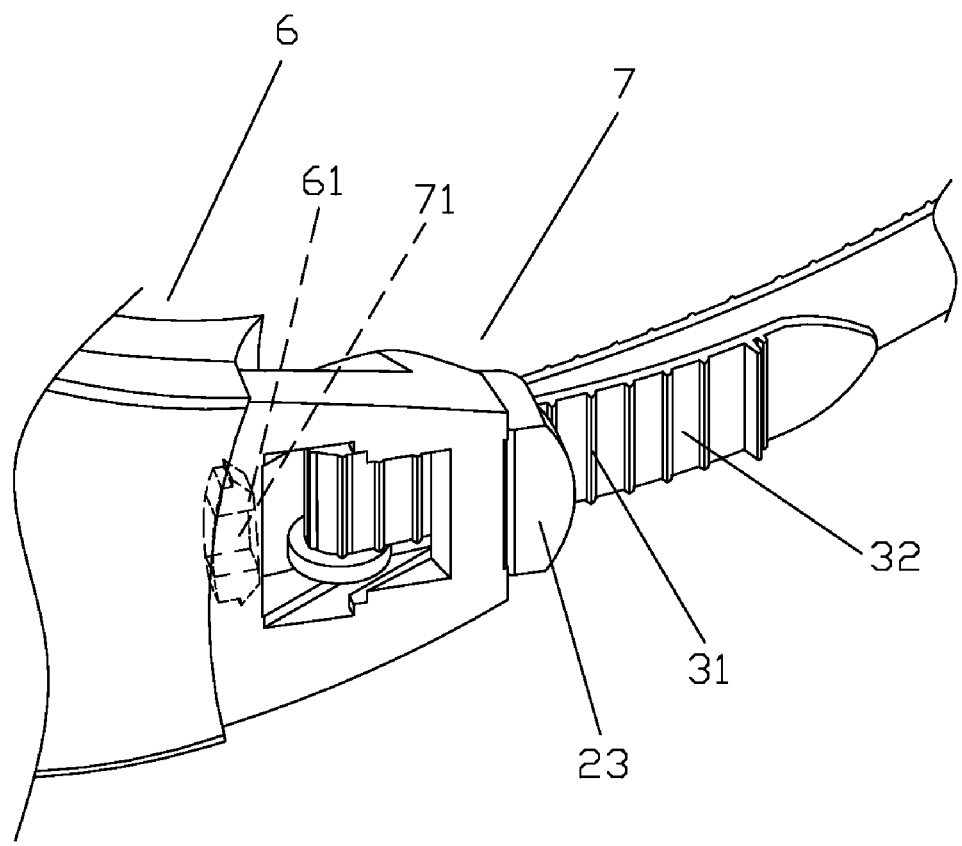
FIG. 9 shows a partial, exploded perspective view of the pair of swimming/diving goggles of FIG. 8.
Figure 10:
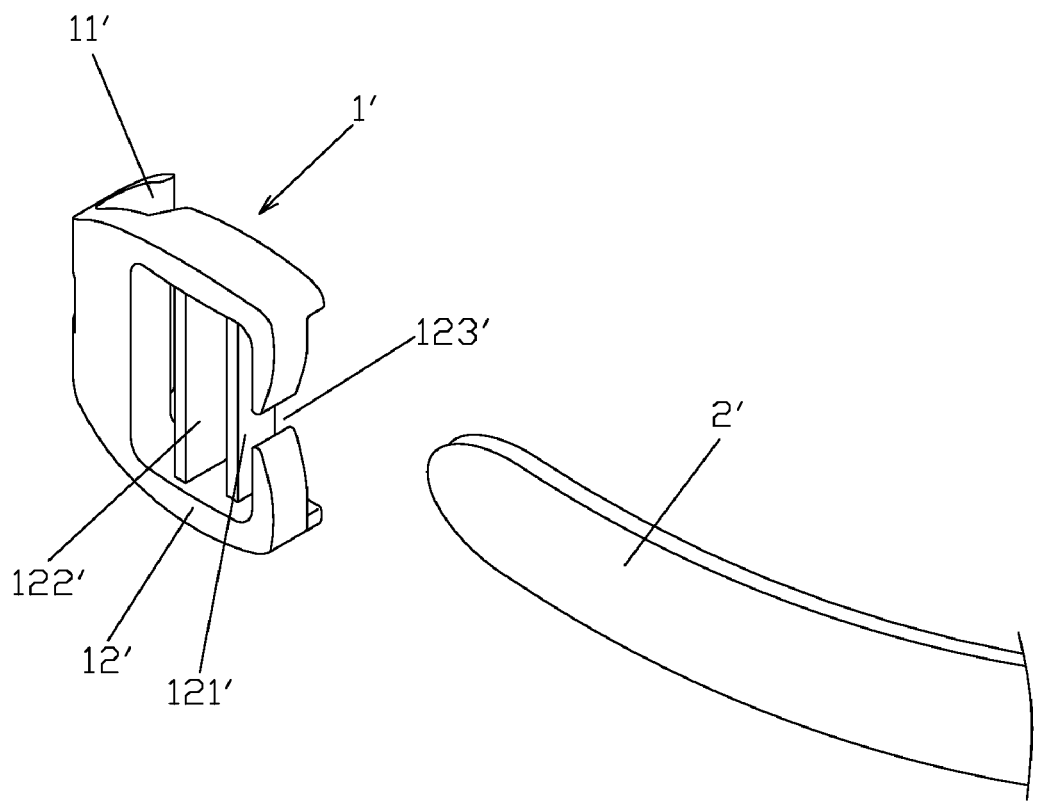
FIG. 10 shows an exploded perspective view of a conventional buckle for swimming/diving goggles.
Figure 11:
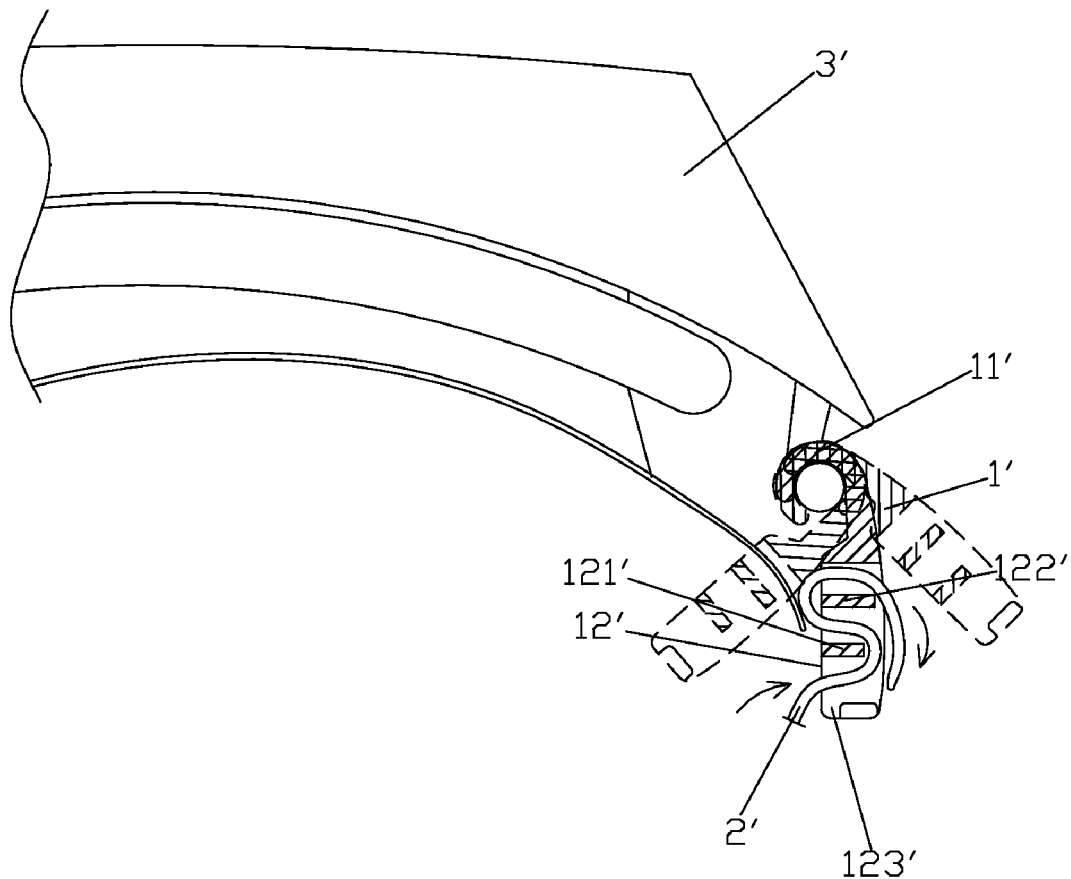
FIG. 11 shows a partial, partially sectioned, top view, of a pair of swimming/diving goggles utilizing the buckle of FIG. 10.
Figure 12:
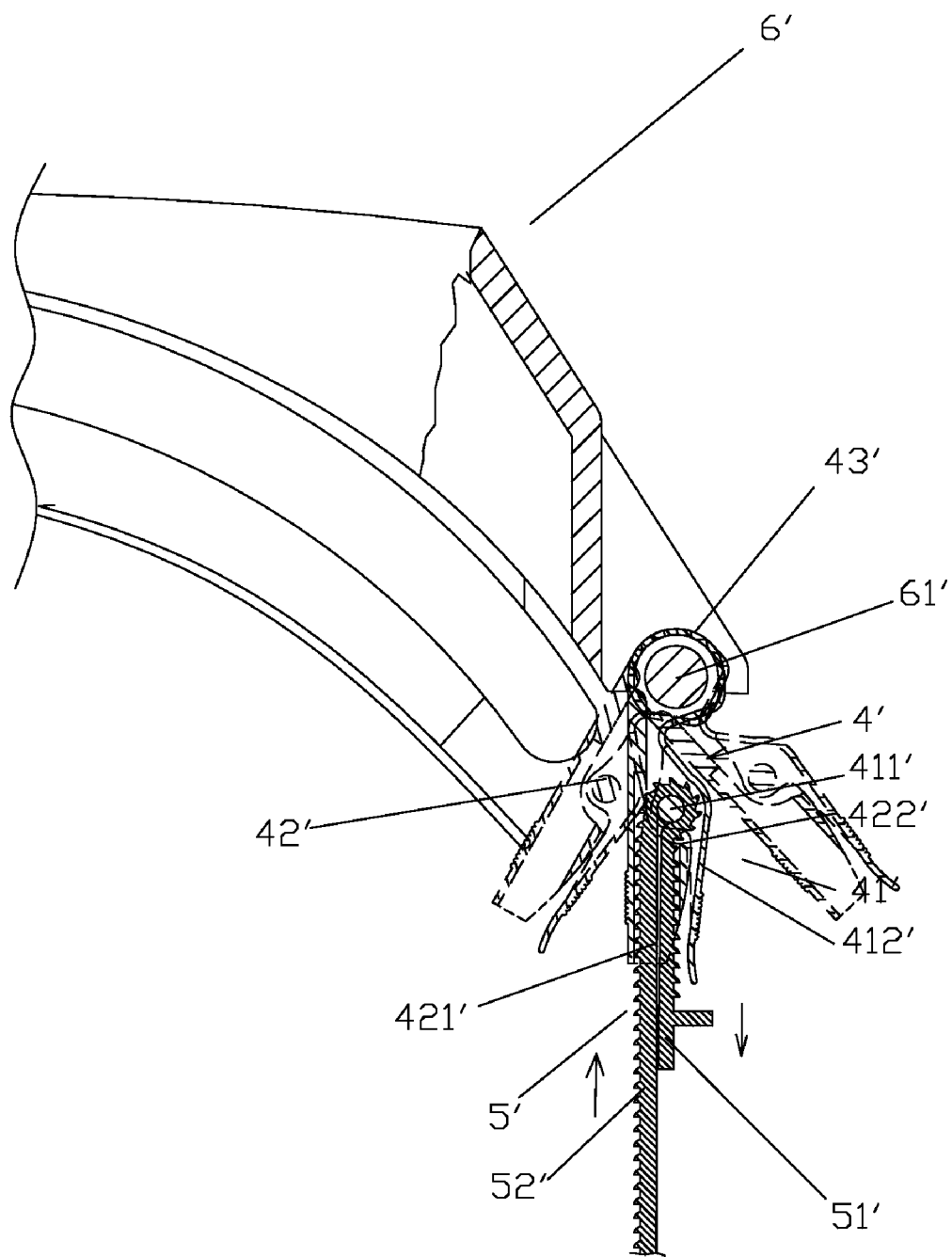
FIG. 12 shows a partial, partly sectioned, top view of another pair of conventional swimming/diving goggles, illustrating tightening of a head strap.
Figure 13:
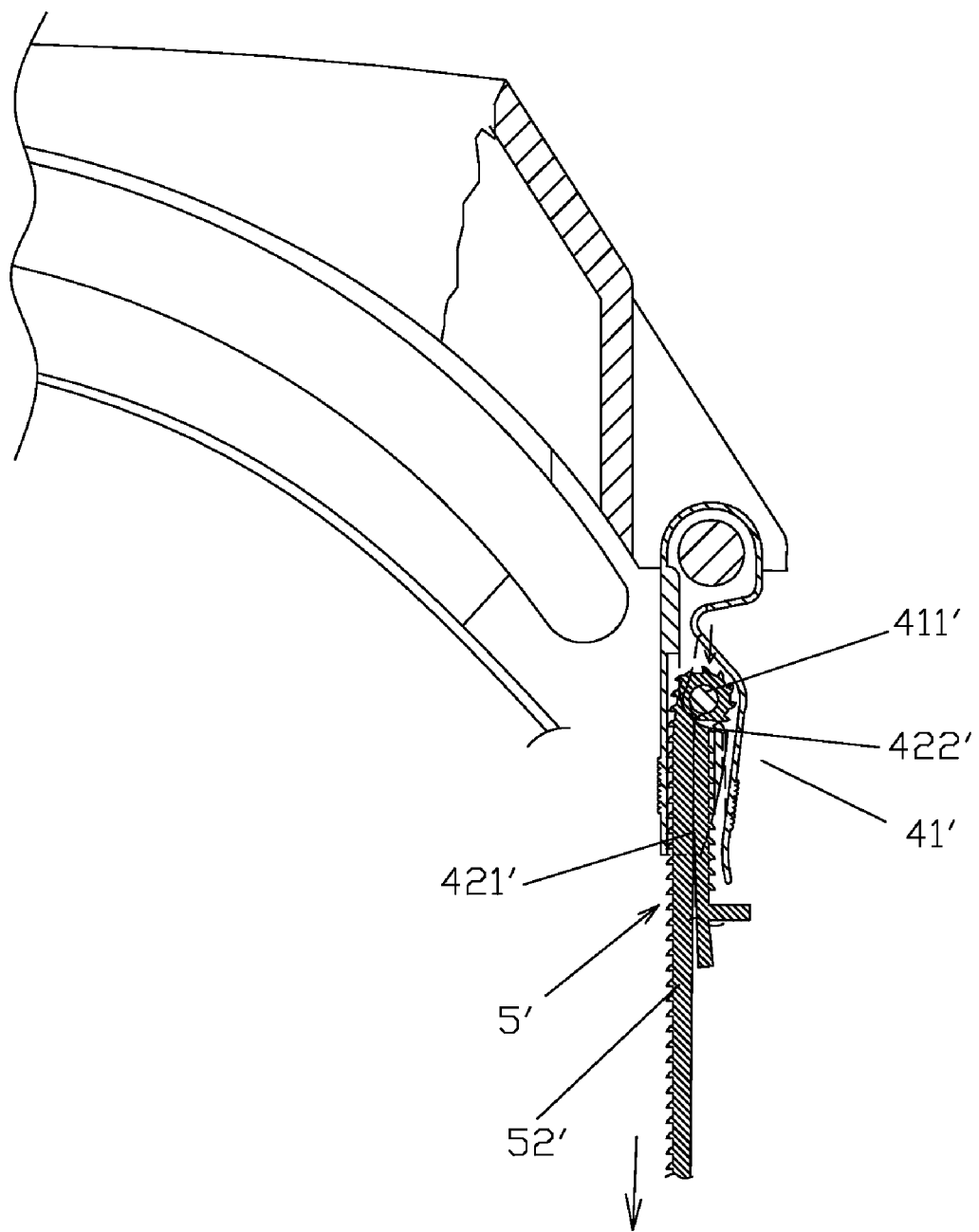
FIG. 13 shows a partial, partly sectioned, top view of the pair of conventional swimming/diving goggles of FIG. 12, illustrating release of the head strap after adjustment.
Figure 14:
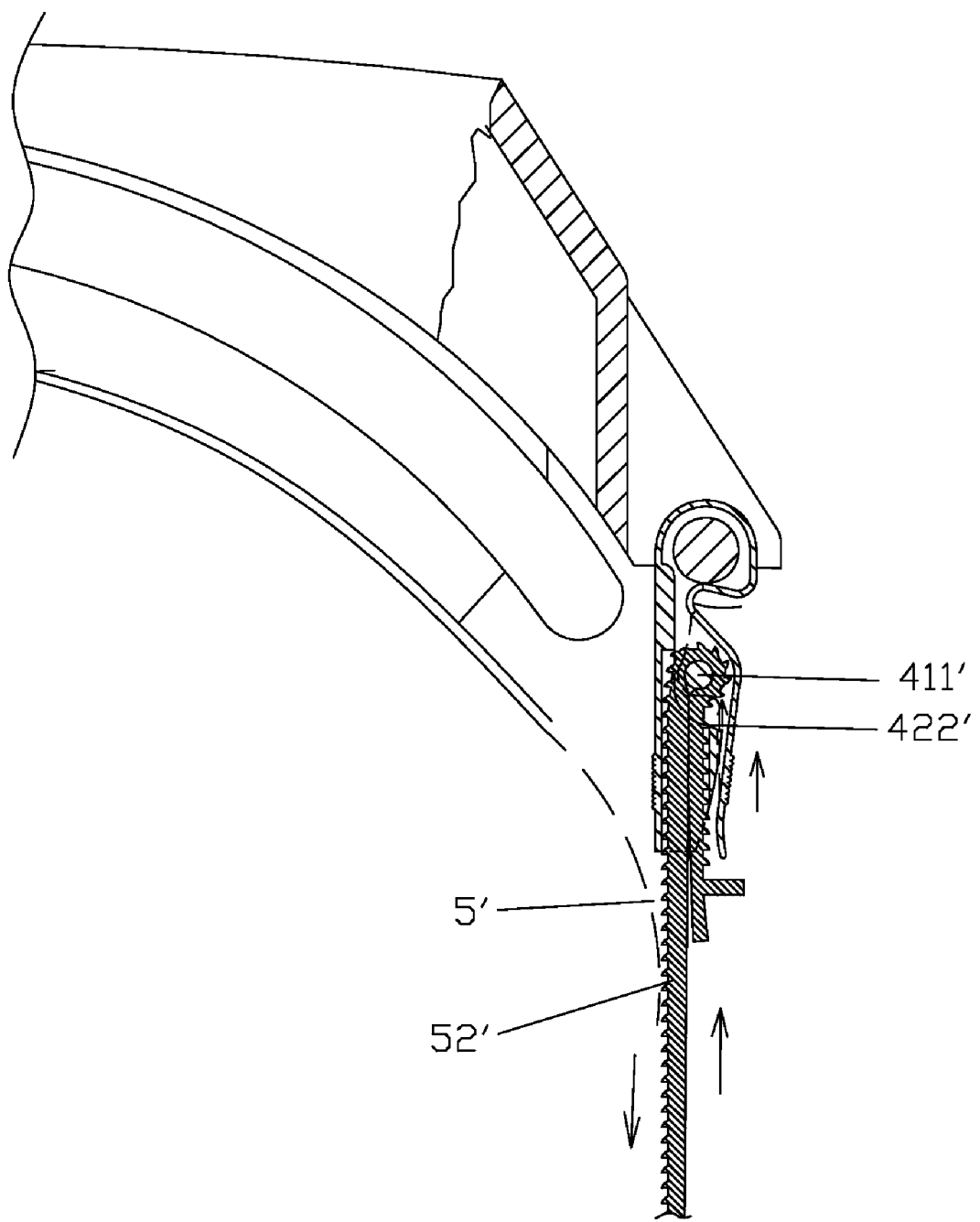
FIG. 14 shows a partial, partly sectioned, top view of the pair of conventional swimming/diving goggles of FIG. 12, illustrating loosening of the head strap by directly moving the head strap.

With reference to FIGS. 8 and 9, the head strap coupling member (now designated by 7) can be a member separate from the main body (now designated by 6). Specifically, the head strap coupling member 7 includes a coupling section 71 releasably coupled with a coupling section 61 on the main body 6. Thus, the coupling member 7 can be selectively mounted to various main bodies of various sizes and shapes. It can be appreciated that the head strap coupling member 7 can be engaged with the main body 6 by gluing or other methods.

In a case that the adjusting block 2 has no operative piece 23 and hence no opening 24, the user can directly press the head strap 3 to urge the board 21 to pivot for the purposes of loosening the head strap 3. The stop edges 132, the stop walls 25, and the cover 4, 5 can be omitted without adversely affecting the clamping effect. The pivots 22 can be substituted by a single pivot or shaft.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

The invention claimed is:

1. A pair of swimming/diving goggles comprising:
a main body including two sides;
two head strap coupling members respectively provided on the two sides of the main body, with each of the two head strap coupling members including a through-hole defined by two lateral walls and an outer end wall;
two adjusting blocks each including a board pivotably mounted in the through-hole of one of the two head strap coupling members, allowing the board to pivot relative to the main body;
a head strap made of a soft, elastic material, with the head strap extending through the through-hole of each of the two head strap coupling members and around the board of each of the adjusting blocks, with a portion of the head strap being located between the outer end wall of the through-hole and the board,
with a spacing between the board of each of the adjusting blocks and the outer end wall of the through-hole of one of the two head strap coupling members being changeable when one of the adjusting blocks is pivoted, allowing the head strap to move to adjust a tightening length of the head strap, and with the head strap exerting a clamping force to clamp the head strap between the board and the outer end wall of the through-hole.

2. The pair of swimming/diving goggles as claimed in claim 1, with the head strap coupling members being integrally formed with the main body as a single continuous monolithic piece.

3. The pair of swimming/diving goggles as claimed in claim 1, with each of the head strap coupling members including a coupling portion, and with each of the two sides of the head strap coupling members including a coupling portion releasably coupled with the coupling portion of one of the head strap coupling members.

4. The pair of swimming/diving goggles as claimed in claim 1, with each of the two lateral walls of the through-hole including a groove, and with the board of each of the adjusting blocks including two pivots respectively and pivotably received in the grooves.

5. The pair of swimming/diving goggles as claimed in claim 1, with the outer end wall of the through-hole of each of the head strap coupling members including a pressing edge having a width smaller than that of the outer end wall, and with the head strap being securely clamped between the pressing edge of each of the head strap coupling members and the board of each of the adjusting blocks.

6. The pair of swimming/diving goggles as claimed in claim 1, with the board of each of the adjusting blocks further including an operative piece extending from an outer end of the board in a direction transverse to the board, and with the operative piece including an opening through which the head strap extends.

7. The pair of swimming/diving goggles as claimed in claim 1, with the board of each of the adjusting blocks further including a stop wall on each of two lateral sides thereof, and with the head strap being located between the stop walls.

8. The pair of swimming/diving goggles as claimed in claim 7, with each of the two lateral walls of the through-hole of each of the two head strap coupling members including a stop edge, with the stop walls of each of the adjusting blocks abutting with the stop edges of one of the two head strap coupling members to restrain the spacing between the outer end wall of the through-hole and the board.

9. The pair of swimming/diving goggles as claimed in claim 1, further comprising a cover mounted to each of the two head strap coupling members and covering the through-hole.

* * * * *